United States Patent [19]
Woodward et al.

[11] Patent Number: 5,942,424
[45] Date of Patent: Aug. 24, 1999

[54] METHOD FOR THE ENZYMATIC PRODUCTION OF HYDROGEN

[75] Inventors: Jonathan Woodward, Kingston, Tenn.; Susan M. Mattingly, State College, Pa.

[73] Assignee: Lockheed Martin Energy Research Corporation, Oak Ridge, Tenn.

[21] Appl. No.: 08/879,243

[22] Filed: Jun. 19, 1997

[51] Int. Cl.$^6$ .................................. C12P 3/00; C12N 9/04
[52] U.S. Cl. ................................. 435/168; 435/190
[58] Field of Search ..................................... 435/168, 190

[56] References Cited

PUBLICATIONS

Biotech Abstract, Woodward et al "Nat. Biotech" (Jul. 1996) 14, 7, 872–874. Equivalent to #7 IDS Jun. 19, 1997.
Biotech Abstract, Mattingly et al "Abstr. Pap. Am. Chem. Soc." (Mar. 24, 1996) 211 Meet. Pt. 2.
Y. Ueno, et al, "Biological Production of Hydrogen from Cellulose by Natural Anaerobic Microflora," *Jl. Fermentation & Bioengineering*, vol. 79, No. 4, 395–397, 1995.
F. Taguchi, et al, "Direct Conversion of Cellulosic Materials to Hydrogen by Clostridium Sp. Strain No. 2," *Enzyme & Microbial Tech* 17:147–150, 1995.
R. Moezelaar, et al, "Fermentation in the Unicellular Cyanobacterium *Microcystis* PCC7806," *Arch. Microbiol.* 162:93–69, 1994.
K. Ma, et al, "Hydrogen Production from Pyruvate by Enzymes Purified from the Hyperthermophilic Archaeon, *Pyrococcus furiosus*: A Key Role for NADPH," *FEMS Microbiol. Ltrs.* 122 245–250, 1994.
J.R. Bright, et al, "Cloning, Sequencing and Expression of the Gene Encoding Glucose Dehydrogenase from the Thermophilic Archaeon *Thermoplasma acidophilum*," *Eur. J. Biochem.*, 211 549–554, 1993.
E. Greenbaum, "Biophotolysis of Water: The Light Saturation Curves," *Photobiochem. and Photobiophys.* 8, 323–332, 1984.
J. Woodward, et al, "In Vitro Hydrogen Production by Glucose Dehydrogenase and Hydrogenase," *Nature Biotechnology*, vol. 14, Jul. 1996.

*Primary Examiner*—Herbert J. Lilling
*Attorney, Agent, or Firm*—Shelley L. Stafford

[57] ABSTRACT

The present invention is an enzymatic method for producing hydrogen comprising the steps of: a) forming a reaction mixture within a reaction vessel comprising a substrate capable of undergoing oxidation within a catabolic reaction, such as glucose, galactose, xylose, mannose, sucrose, lactose, cellulose, xylan and starch. The reaction mixture further comprises an amount of glucose dehydrogenase in an amount sufficient to catalyze the oxidation of the substrate, an amount of hydrogenase sufficient to catalyze an electron-requiring reaction wherein a stoichiometric yield of hydrogen is produced, an amount of pH buffer in an amount sufficient to provide an environment that allows the hydrogenase and the glucose dehydrogenase to retain sufficient activity for the production of hydrogen to occur and also comprising an amount of nicotinamide adenine dinucleotide phosphate sufficient to transfer electrons from the catabolic reaction to the electron-requiring reaction; b) heating the reaction mixture at a temperature sufficient for glucose dehydrogenase and the hydrogenase to retain sufficient activity and sufficient for the production of hydrogen to occur, and heating for a period of time that continues until the hydrogen is no longer produced by the reaction mixture, wherein the catabolic reaction and the electron-requiring reactions have rates of reaction dependent upon the temperature; and c) detecting the hydrogen produced from the reaction mixture.

10 Claims, 8 Drawing Sheets

| | Glucose (mM) | | | Galactose (mM) | | | Xylose (mM) | | | Mannose (mM) |
|---|---|---|---|---|---|---|---|---|---|---|
| | 5 | 50 | 250 | 5 | 50 | 250 | 5 | 50 | 250 | 50 |
| Start pH | 7.45 | 7.46 | 7.44 | 7.49 | 7.36 | 7.43 | 7.34 | 7.43 | 7.41 | 7.52 |
| End pH | 7.07 | 6.27 | 4.13 | 7.10 | 6.16 | 3.94 | 7.07 | 6.68 | 5.88 | 7.42 |
| % Yield[1] (μmol $H_2$) | 76.5 (7.65) | 100 (100) | 19 (95.9) | 100 (10) | 100 (100) | 20.6 (103.2) | 100 (10) | 52.8 (52.8) | 15.9 (79.4) | 9.8 (9.8) |
| Max. rate (μmol h$^{-1}$) | 4.1 | 50.3 | 42.6 | 10.3 | 82.9 | 16.8 | 3.1 | 7.0 | 13.1 | 0.81 |

[1]Based on stoichiometry of 1 mol $H_2$/mol sugar.

Fig. 6

| Renewable | Rate ($\mu$mol h$^{-1}$) | Yield (%) | Maximum yield (Y/N) |
|---|---|---|---|
| Lactose[a] | 6.3 | 37.2 | N |
| Sucrose[a] | 2.8 | 25.5 | N |
| Cellulose/Xylan[b] | 4.5 | 22.3 | N |
| Starch[b] | 8.1 | 16.0 | Y |
| Steam-exploded aspen[b] | 3.4 | 39.2 | Y |

[a] Substrate concentration used 100 $\mu$mol in 2.0-mL reaction volume.
[b] Substrate concentration used 111 $\mu$mol glucose/xylose equivalent.
Other reaction mixture conditions were standard and included 0.63 unit lactase, 0.48 unit invertase, 38.6 units avicelase, 10 units of amyloglucosidase for the hydrolysis of lactose, sucrose, cellulose/xylan, and steam-exploded aspen starch, respectively.

Fig. 7

| Substrate (100 mM) | Maximum rate ($\mu$mol h$^{-1}$) | Hydrogen yield (% Theor. Max.) |
|---|---|---|
| Glucose | 50.3 | 100.0 |
| Galactose | 82.9 | 100.0 |
| Xylose | 7.0 | 52.8 |
| Mannose | 0.8 | 9.8 |
| 2-Deoxyglucose | 3.6 | 34.9 |
| Fructose | 0.0 | 0.0 |

METHOD FOR THE ENZYMATIC PRODUCTION OF HYDROGEN

This invention was made with Government support under contract DE-AC05-96OR22464 awarded by the Office of Utility Technologies, Advanced Utility Concepts Division, U.S. Department of Energy to Lockheed Martin Energy Research Corporation, the Government has certain rights in this invention.

FIELD OF THE INVENTION

The present invention relates to a method for the production of hydrogen from sources such as glucose, galactose, xylose, mannose, cellulose, sucrose, lactose, xylan and starch and more particularly to a method for the in vitro enzymatic production of hydrogen from such sources as glucose, galactose, xylose, mannose, cellulose, sucrose, lactose, xylan and starch.

BACKGROUND OF THE INVENTION

The use of hydrogen as an alternative fuel source is receiving wide attention in both political and technical arenas. One reason for this attention lies in the ability of hydrogen to burn cleanly without producing any toxic by-products. Hydrogen is a clean and renewable energy resource, not contributing to the greenhouse effect. Biological production of hydrogen using wastewater and other biomass as raw materials has been attracting attention as an environmentally friendly process that does not consume fossil fuels. An area of concern in the use of hydrogen as a fuel source is in developing an efficient, economical method of production in which unwanted coproducts are not produced. Gasification, pyrolysis, and fermentation of biomass have been, and are being considered as potential routes to hydrogen production.

Hydrogen production by microorganisms can be divided into two main categories: one is by photosynthetic bacteria cultured under anaerobic light conditions, and the other is by other anaerobic bacteria. The latter possess the ability to produce hydrogen without photoenergy. There have been many studies on the conversion of biomass to hydrogen by anaerobic bacteria. There have also been studies on the development of hydrogen production during the treatment process of organic wastewater using anaerobic bacteria. Hydrogen production by anaerobic microflora has been reported by Minoda et al and Sykes and Kirsch. In their experiments, hydrogen production resulted from inhibition of methane formation from hydrogen, and microflora which produces hydrogen with high efficiency has not been obtained. In a study by Yoshiyuko Ueno et al, experiments were carried out in order to select the anaerobic microflora suitable for the production of hydrogen with a medium containing cellulose as a model of wastewater.

Plant biomass such as agricultural residues and bioindustrial wastes contains high percentages of cellulose and hemicellulose, and represents one of the most abundant renewable energy sources. On the other hand, little interest has been focused on biologic conversion of cellulosic materials present in biomass to high-value hydrogen. To convert biomass to hydrogen, the full use of pentoses in addition to hexoses in hydrolysates of cellulose and hemicellulose is important. Because Clostridium sp. strain no. 2, isolated from termites, has been found to convert arabinose and xylose to hydrogen more efficiently than glucose, studies led Fumiaki Taguchi et al to investigate direct hydrogen production by a combination procedure in one flask consisting first of enzymatic hydrolysis of cellulose and hemicellulose, and second, hydrogen fermentation of the hydrolysates by strain no. 2.

OBJECTS OF THE INVENTION

Accordingly, it is an object of the present invention to provide a new efficient and economical method for the production of hydrogen.

It is another object of the present invention to provide a new efficient and economical in vitro method for the enzymatic production of hydrogen.

It is yet another object of the present invention to provide a new efficient and economical in vitro method for the enzymatic production of hydrogen without the production of unwanted coproducts.

Further and other objects of the present invention will become apparent from the description contained herein.

SUMMARY

In accordance with one aspect of the present invention, the foregoing and other objects are achieved by an enzymatic method for producing hydrogen comprising the steps of: a) forming a reaction mixture within a reaction vessel, the reaction mixture comprising an amount of substrate capable of undergoing oxidation within a catabolic reaction, the substrate in an amount sufficient for the production of hydrogen to occur in a stoichiometric yield, an amount of glucose dehydrogenase in an amount sufficient to catalyze the oxidation of the substrate, an amount of hydrogenase sufficient to catalyze an electron-requiring reaction whereby the stoichiometric yield of hydrogen is produced, an amount of Ph buffer in an amount sufficient to provide an environment that allows the hydrogenase and the glucose dehydrogenase to retain sufficient activity for the production of hydrogen to occur, and an amount of nicotinamide adenine dinucleotide phosphate sufficient to transfer electrons from the catabolic reaction to the electron-requiring reaction; b) heating the reaction mixture at a temperature sufficient for glucose dehydrogenase and hydrogenase to retain sufficient activity and at a temperature sufficient for the production of hydrogen to occur and heating for a period of time that continues until hydrogen is no longer produced by the reaction mixture, wherein the catabolic reaction and the electron-requiring reaction have rates of reaction dependent upon the temperature; and c) detecting the hydrogen produced from the reaction mixture.

BRIEF DESCRIPTION OF THE DRAWINGS

For a better understanding of the present invention, together with other and further objects, advantages and capabilities thereof, reference is made to the following disclosure and appended claims when read in connection with the appended drawings, wherein:

FIG. 6 shows a comparison of rates and yields of hydrogen production from sugars as a function of concentration.

FIG. 7 shows rates and yields of hydrogen production from renewables.

FIG. 8 shows the sugar specificity of *Thermoplasma acidophilum* glucose dehydrogenase in hydrogen production.

DETAILED DESCRIPTION OF THE INVENTION

Figure 1:
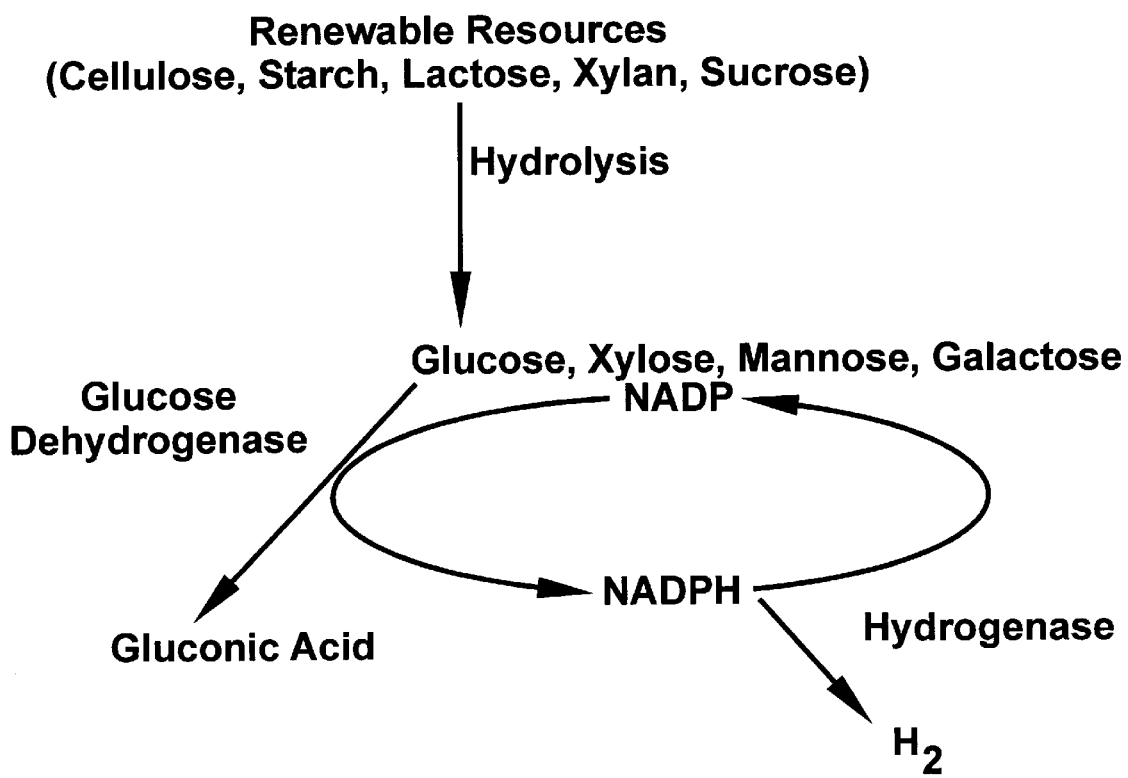
FIG. 1 illustrates the reaction pathway for the enzymatic conversion of renewable resources to hydrogen.

The present invention is an in vitro enzymatic method for the generation of hydrogen from a substrate such as glucose, galactose, xylose, mannose, cellulose, sucrose, lactose, xylan and starch. Specific enzymes are used to breakdown the substrate and convert it to glucose, with the exception of galactose, xylose and mannose which are already monosaccharide sugars like glucose, then hydrogen production is based on two reactions. The first is the action of an enzyme, glucose dehydrogenase (GDH), on the monosaccharide sugar- glucose, xylose, galactose or mannose that results in the oxidation of that sugar. The GDH catalyzes the oxidation of the sugar to glucono-ò-lactone, which hydrolyzes to gluconic acid. Then, the second reaction requires the removal of electrons from the glucose, galactose, xylose or mannose and transfers the electrons to the cofactor of GDH, nicotinamide adenine dinucleotide phosphate (NADP). The reduced NADP (NADPH) is then interacted with another enzyme, hydrogenase to produce stoichiometric yields of hydrogen while attaining the highest achievable rate of evolution of the gas. Liquid hydrogen may also be produced. The cofactor is either $NAD^+$ or $NADP^+$, which is reduced. Although most hydrogenases from microbial sources do not interact with physiological electron carriers such as NADPH because of its insufficient low-potential, two hydrogenases, one from the aerobic bacterium *Alcaligenes eutrophus* and the other from the anaerobic archaeon *Pyrococcus fuiosus*, have been shown to use NADPH as an electron donor. Continuous regeneration and recycling of $NADP^+$, as well as enzyme stability, is essential for prolonged hydrogen generation. This method of the present invention is beneficial because glucose is derived from such sources as cellulose, starch, xylan, lactose and sucrose which are an abundant and renewable resource and the only other product in this reaction, gluconic acid, is a commodity chemical. FIG. 1 shows the enzymatic pathway for the conversion of renewable resources to hydrogen. It can be seen from FIG. 1 that cellulose, starch, xylan, lactose and sucrose all undergo hydrolysis to produce glucose, xylose, mannose and/or galactose. Glucose, xylose, mannose and galactose are monosaccharide sugars that undergo oxidation by glucose dehydrogenase to gluconic acid. Then, electrons are transferred from the monosaccharide sugar to NADP and the cycle continues with the production of hydrogen.

GDH and hydrogenase have been purified from *Thermoplasma acidophilum* and *P. fuiiosus*, which are thermophilic Archaea (formerly Archaebacteria) that grow optimally at 59° C. and 100° C. respectively.

*T. acidophilum* GDH and *P. furiosus* hydrogenase were purified enzymes obtained from the University of Bath and the University of Georgia, respectively. *T. acidophilum* GDH can now be commercially obtained from Sigma Chemical Company, St. Louis, Mo. The gene for *T. acidophilum* glucose dehydrogenase was cloned, sequenced, and expressed in *Escherichia coli* from which the enzyme was purified and assayed as described in 1989 in *The Biochemical Journal* volume 261, pp. 973–977 by L. D. Smith et al. and as described by J .R. Bright et al. in 1993 in the *European Journal of Biochemistry* v. 211, pp. 549–554. The enzyme possessed a specific activity of 420 units/mg protein where 1 unit is defined as the amount of enzyme required to produce 1 µmol NADPH/min at 55° C. and pH 7.0. Hydrogenase from *P. furiosus* was purified, as described by F. O. Bryant and M. W. W. Adams in 1989 in the *Journal of Biological Chemistry*, volume 264, pp. 5070–5079, and assayed by measuring hydrogen evolution from reduced methyl viologen in 50 mM Tris, pH 0, containing 1 mM sodium dithionite at 80 ° C. Its activity was measured at 1005 units/ml. $\beta$-$NADP^{30}$ was purchased from Sigma Chemical Company (St. Louis, Mo.). β-D-Glucose was purchased from Calbiochem (San Diego, Calif.). Cellulase (Novozyme 342, an alkaline cellulase produced by *Humicola insolens*) was obtained from Novo Nordisk (Franklinton, N.C). Prior to its use, it was gel filtered; the filtered enzyme has a protein concentration of 20 mg/ml. Also, β-D-glucose, *Bacillus megaterium* GDH, $NADP^+$, and NADPH were commercial preparations obtained from Sigma Chemical Company. *B. megaterium* GDH was stored at 4° C. in a 3M NaCl 50 mM sodium phosphate buffer solution at pH 6.5 for stability.

The activities (units/mL) of GDH and hydrogenase were determined for pH 5.0–8.0 in 50 mM sodium phosphate buffer; additional measurements for hydrogenase at pH 8.5 and 9.0 were performed in 50 mM Tris-HCl buffer. Known quantities of *P. furiosus* hydrogenase and *T. acidophilum* GDH were diluted in ultrapure water, while *B. megaterium* GDH was diluted in 1M NaCl 50 mM sodium phosphate buffer pH 6.5, prior to measurement of activity.

Figure 2:
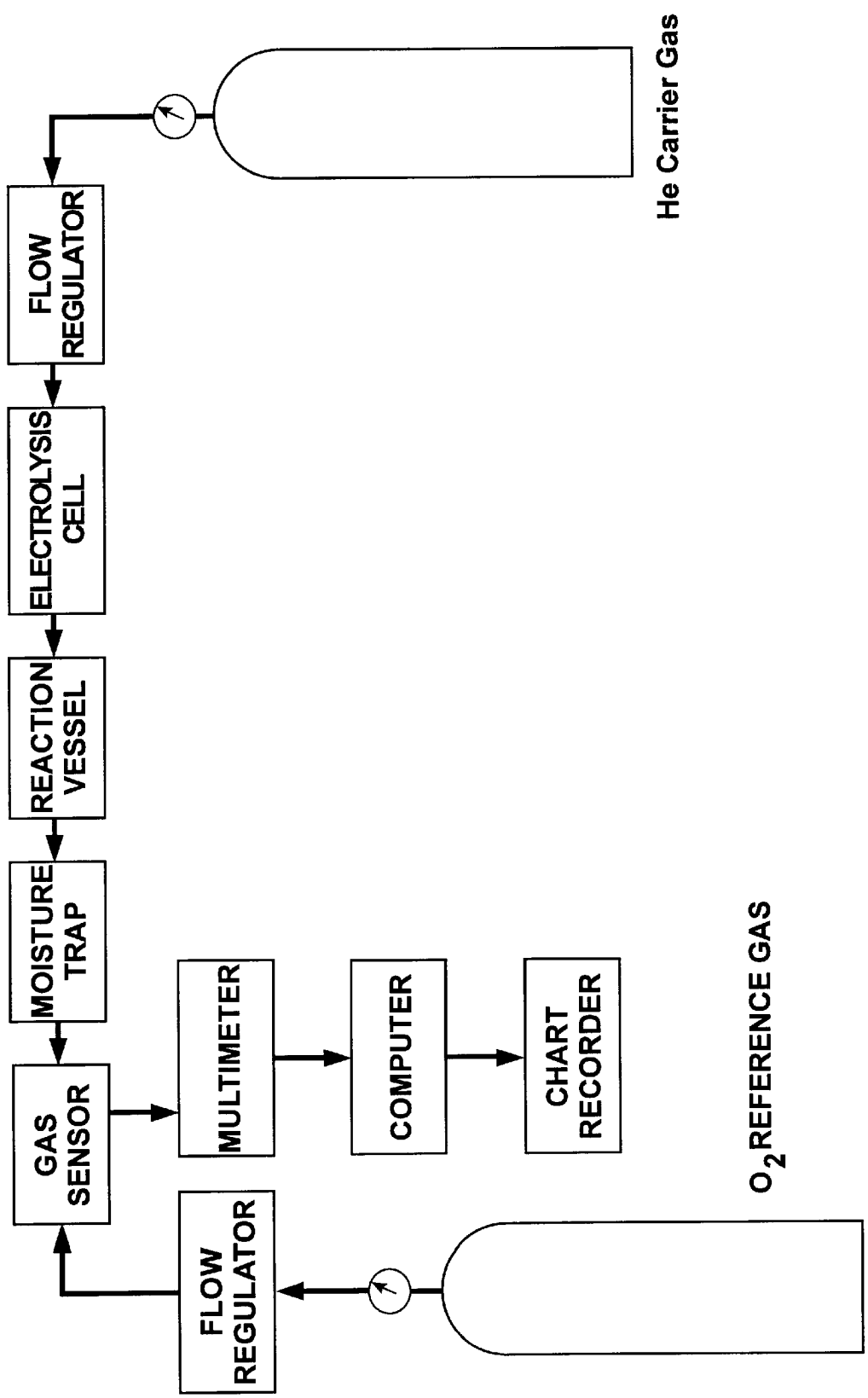
FIG. 2 is a schematic illustration of the apparatus used to measure hydrogen production.

The apparatus used for the measurement of hydrogen production was a continuous flow system shown in FIG. 2. The detection system of this apparatus is described in detail by E. Greenbaum in 1984 in *Photobiochemistry and Photobiophysics*, volume 8, pp. 323–332, incorporated herein by reference. The reaction vessel containing the enzymes, cofactor and substrate in a 2.0 ml volume was continuously purged with helium and calibrated with an inline electrolysis cell and Faraday's law of electrochemical equivalence connected in tandem with the hydrogen detection system. The inline electrolysis cell produced a known amount of hydrogen to be delivered to the detector for calibration. The reaction vessel used was a standard pyrex laboratory glass vessel thermojacketed to allow water to circulate around the vessel during the reaction in order to evenly distribute the heat within the reaction vessel. Any vessel can be used for the reaction vessel such as glass, pyrex glass, ceramic material, metal, etc., as long as the vessel is used in a closed system. The hydrogen detection system comprised a combustible gas analyzer (Bio-Gas Detector Corporation, Okemos, Mich.) consisting of a Figaro semiconductor tin oxide gas sensor. A voltage increase occurred across the sensor when a combustible gas came into contact with the sensor surface, due to a decrease in the sensor resistance. This was measured by a Keithley Model 2000 multimeter (Cleveland, Ohio). Current was measured with a Keithley Model 485 picoammeter. Data was analyzed using ASYST Technologies, Inc., 4.0 Analysis Software (Rochester, N.Y.).

Measurements of the enzyme activity were recorded spectrophotometrically at 340 nm at 25° C. using a Varian Cary 219 spectrophotometer. GDH activity was determined by tracking $NADP^+$ reduction over time in a 1.0 mL reaction mixture containing the diluted enzyme, 10 mM glucose, and 1 mM $NADP^+$ in buffer. Hydrogenase activity was similarly determined by tracking NADPH oxidation over time in a 1.0 mL reaction mixture containing the diluted enzyme and 0.1 mM NADPH in buffer.

From FIG. 2 helium passed through the electrolysis cell, picking up the known amount of generated hydrogen for calibration purposes, and then passed through the reaction vessel, picking up an unknown amount of generated hydrogen from the reaction mixture. The gaseous mixture then passed through a moisture trap to absorb any moisture present in the helium stream. Then, the helium carrying the hydrogen molecules flowed to the moisture-sensitive gas sensor for detection and analysis.

The reaction mixture comprises an amount of substrate which is capable of undergoing oxidation within a catabolic reaction, such as cellulose, xylan, sucrose, lactose and starch, which have hydrolyzed to glucose, and mannose, galactose, xylose. The substrate is in an amount sufficient enough for the production of hydrogen to occur in stoichiometric yields. The reaction mixture also comprises a sufficient amount of the necessary enzymes in order to hydrolyze cellulose, xylan, sucrose, starch and lactose into their monosaccharide sugars, such as cellulase (for the hydrolysis of cellulose and xylan), invertase (for hydrolysis of sucrose), amyloglucosidase (for hydrolysis of starch) and lactase (for hydrolysis of lactose). The reaction mixture further comprises an amount of glucose dehydrogenase in an amount sufficient enough to catalyze the oxidation of the substrate, an amount of hydrogenase sufficient enough to catalyze an electron-requiring reaction whereby the stoichiometric yields of hydrogen are produced, an amount of pH buffer in an amount sufficient enough to provide an environment that allows the hydrogenase and the glucose dehydrogenase to retain sufficient activity for the production of hydrogen to occur. The reaction mixture also comprises an amount of NADP sufficient enough to transfer electrons from the catabolic reaction to the electron-requiring reaction in order that hydrogen is produced.

EXAMPLE 1

The reaction mixture (2.0 ml) consisting of 50 mM sodium phosphate buffer at pH 7.0, containing 10 $\mu$mol glucose, 26 units of hydrogenase, 12.6 units of GDH, and 1 $\mu$mol of $NADP^+$ was placed in a standard laboratory glass pyrex vessel having a thermojacket and heated at 50° C. The reaction was started by the addition of $NADP^+$ and hydrogen evolution was immediately observed. After 18 hours, another 10 $\mu$mol of glucose was added to the reaction mixture. The reaction vessel was continuously heated at 50° C. until no more hydrogen was produced from the reaction mixture.

Figure 3:
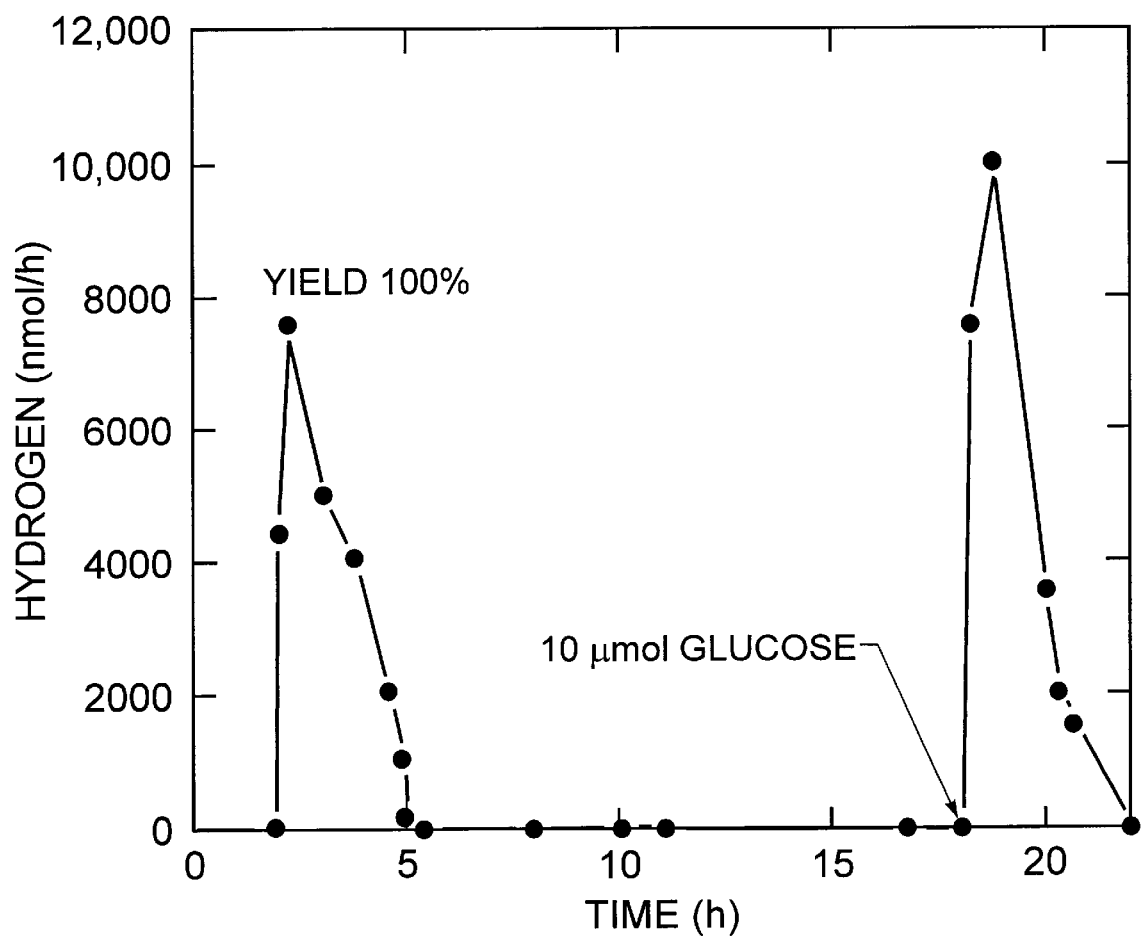
FIG. 3 shows hydrogen production from glucose using T. acidophilum glucose dehydrogenase and P. furiosus hydrogenase at 50° C. according to the conditions of EXAMPLE 1.

The integrated yield of hydrogen (10 $\mu$mol) generated from glucose represented the maximum stoichiometric yield possible, and the rate of hydrogen production reached a maximum (7.5 $\mu$mol) within minutes following initiation of the experiment by the addition of $NADP^+$, as shown in FIG. 3. Hydrogen evolution was reduced to zero after 3 hours; however, when another 10 $\mu$mol of glucose was added to the reaction mixture several hours later, immediate evolution of hydrogen occurred and maximum yield of hydrogen was obtained again. The rate-limiting step in this pathway was the glucose concentration since the concentration of $NADP^+$ used in this example was 0.5 mM, about five times the reported $K_m$ value for this GDH. The presence of 10 mM gluconic acid in the reaction mixture did not affect the rate or yield of hydrogen production; therefore, gluconic acid does not appear to be an inhibitor of this enzyme-coupled process under these conditions. $NADP^+$ was stable at 50° C. for at least 20 hours.

EXAMPLE 2

The reaction mixture (2.0 ml) consisting of 50 mM sodium phosphate buffer at pH 7.0, containing 100 $\mu$mol glucose, 20.7 units of hydrogenase, 12.6 units of GDH, and 1 $\mu$mol of $NADP^+$ was placed in a standard laboratory glass pyrex vessel having a thermojacket and heated at 40° C. The reaction was started by the addition of $NADP^+$ and hydrogen evolution was immediately observed. After 18 hours, another 100 $\mu$mol of glucose was added to the reaction mixture. The reaction vessel was continuously heated at 40° C. until no more hydrogen was generated from the reaction mixture.

Figure 4:
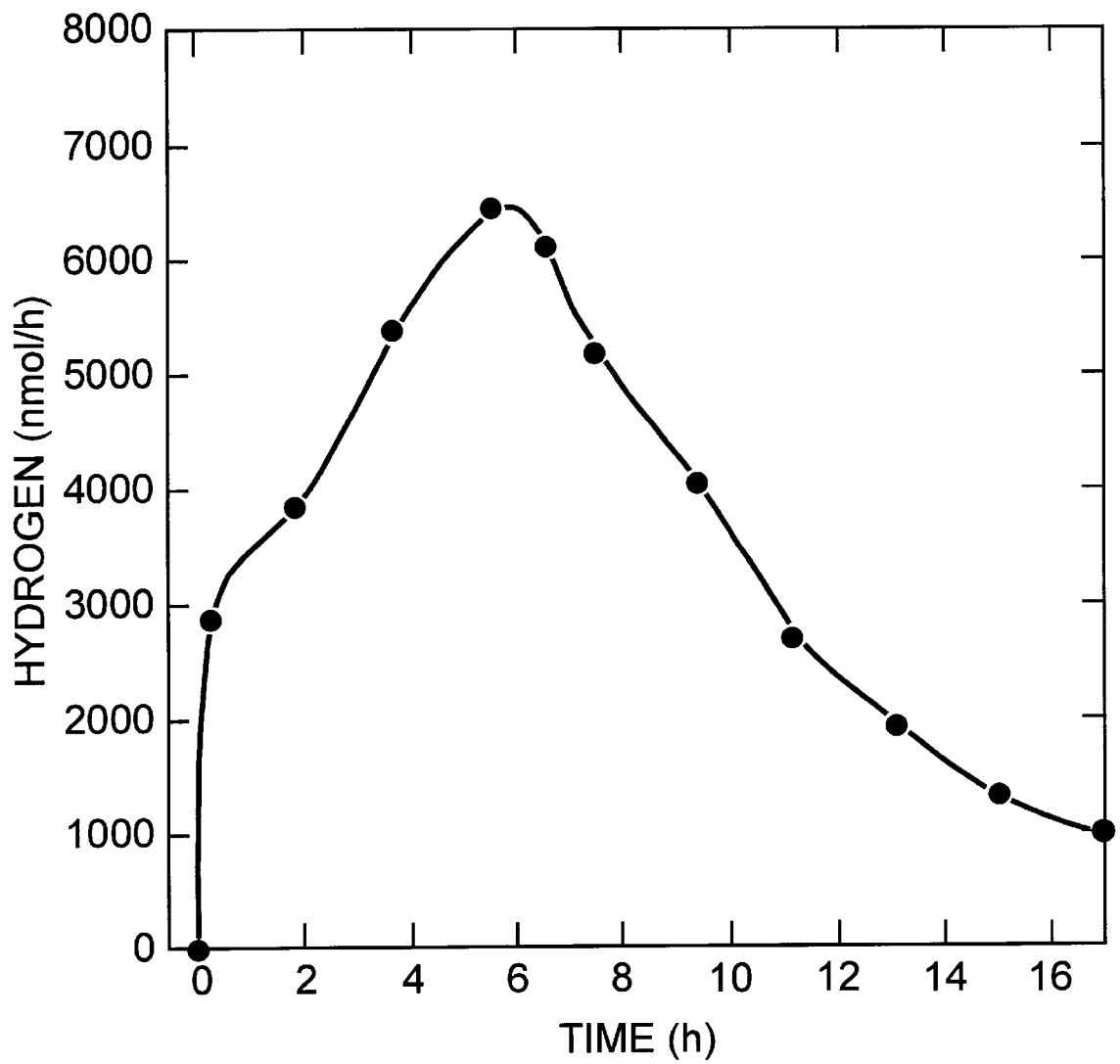
FIG. 4 shows continuous hydrogen production from glucose at 40° C. according to the conditions of EXAMPLE 2.

In Example 2, approximately 64 $\mu$mol of hydrogen had been generated as shown in FIG. 4. At this concentration of glucose, there was a burst of hydrogen evolution during the first few minutes of the reaction followed by a gradual rise to a maximum rate of 6.5 $\mu$mol/h at 6 hours. After this time, the rate started to decline, due to the reaction in glucose concentration. The lower maximum rate of hydrogen evolution as compared with that observed in Example 1, was due to the lower reaction temperature used (40° C.). $NADP^+$ could be reduced and reoxidized at least 64 times without apparent loss in its ability to shuttle electrons from glucose to hydrogenase. Although the pH of the reaction mixture had dropped from pH 7.0 to pH 5.85 after 16 hours, both enzymes retained significant activity. At 40° C. there was little difference between the activity of hydrogenase at pH 5.5 and pH 7.0. The optimum temperature for this enzyme has been determined to be 85° C. with NADPH as the substrate. The activity of GDH at pH 6.0 was determined to be about 50% of its optimal activity at pH 7.0. The loss of enzyme stability under these conditions, however, cannot be discounted. GDH and hydrogenase are composed of four identical and four nonidentical subunits, respectively. GDH from *T. acidophilum* is stable at room temperature in 50% methanol, acetone, or ethanol and in 4M urea for 6 hours. Such stability suggests that the oligomeric structure is unlikely to dissociate under the conditions previously described, especially since this enzyme naturally functions under extreme environmental conditions. Hydrogenase is remarkably stable even at 80° C. with a half-life at 100° C. of 2 hours in vitro.

Cellulose is the most abundant source of glucose and can be hydrolyzed to glucose by the action of cellulases. In EXAMPLE 3, cellulose was converted to hydrogen when cellulase was present in the reaction mixture.

EXAMPLE 3

The reaction mixture (2.0 mL) consisting of 50 mM sodium phosphate buffer, pH 7.0, containing 40 mg of microcrystalline cellulose (Avicel) no glucose, 0.4 mg of cellulase protein (Novozym 342-an alkaline cellulase produced by *Humicola insolens* obtained from Novo Nordis, Franklinton, N.C. and subjected to gel filtration), 26 units of hydrogenase, 12.6 units of GDH and 1 $\mu$mol of $NADP^+$ was placed in a standard laboratory glass pyrex vessel having a thermojacket and heated at 50° C. for about 22 hours. The reaction was started by the addition of $NADP^+$. The reaction vessel was continuously heated at 50° C. until no more hydrogen was generated from the reaction mixture.

Figure 5:
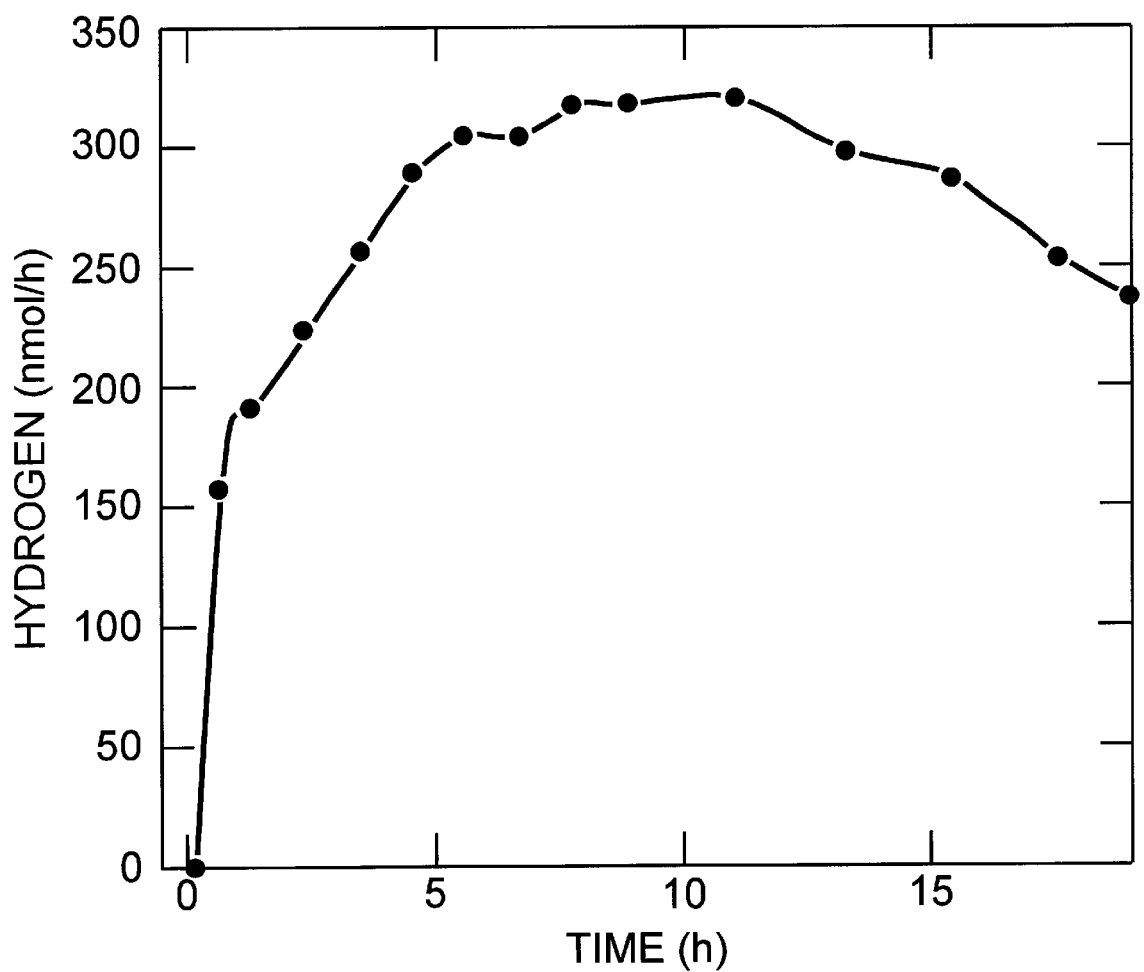
FIG. 5 shows hydrogen production from microcrystalline cellulose as described in EXAMPLE 3.

The data in FIG. 5 show that cellulose was converted to hydrogen as long as cellulase was present in the reaction mixture. Cellulase catalyzed the hydrolysis of cellulose to glucose. The maximum rate of hydrogen evolution was approximately 325 nmol/h, and after 22 hours, the stoichiometric yield of hydrogen was approximately 2.6%. The rate-limiting step in this reaction was the rate of glucose formation from cellulose, since addition of another 400 μg of cellulase to the reaction mixture caused an immediate increase in the rate of hydrogen evolution and consequently, the stoichiometric yield.

Other sources of hydrogen include starch, lactose, galactose, xylose, mannose and sucrose. Starch and lactose both can easily be hydrolyzed to glucose by the action of amylase/amyloglucosidase and lactase, respectively.

FIG. 6 gives data comparing rates and yields of hydrogen production from glucose, galactose, xylose and mannose as a function of concentration. Each sugar was reacted at concentrations of 5 mM, 50 mM, and 250 mM in a 2.0 mL volume of reaction mixture as reflected in EXAMPLES 4–13.

EXAMPLE 4

The reaction mixture (2.0 ml) consisting of 50 mM sodium phosphate buffer at starting pH 7.45, containing 1.8 mg glucose (5 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 7.07.

EXAMPLE 5

The reaction mixture (2.0 ml) consisting of 50 mM sodium phosphate buffer at starting pH 7.46, containing 18 mg glucose (50 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 6.27.

EXAMPLE 6

The reaction mixture (2.0 ml) consisting of 50 mM sodium phosphate buffer at starting pH 7.44, containing 90 mg glucose (250 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 4.13.

EXAMPLE 7

The reaction mixture (2.0 ml) consisting of 50 mM sodium phosphate buffer at starting pH 7.49, containing 1.8 mg galactose (5 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 7.10.

EXAMPLE 8

The reaction mixture (2.0 ml) consisting of 50 mM sodium phosphate buffer at starting pH 7.36, containing 18 mg galactose (50 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 6.16.

EXAMPLE 9

The reaction mixture (2.0 ml) consisting of 50 mM sodium phosphate buffer at starting pH 7.43, containing 90 mg galactose (250 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 3.94.

EXAMPLE 10

The reaction mixture (2.0 ml) consisting of 50 mM sodium phosphate buffer at starting pH 7.34, containing 1.8 mg xylose (5 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 7.07.

EXAMPLE 11

The reaction mixture (2.0 ml) consisting of 50 mM sodium phosphate buffer at starting pH 7.43, containing 18 mg xylose (50 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 6.68.

EXAMPLE 12

The reaction mixture (2.0 ml) consisting of 50 mM sodium phosphate buffer at starting pH 7.41, containing 90 mg xylose (250 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed. The reaction vessel was continuously heated at 50° C. until no more hydrogen was produced from the reaction mixture. The ending pH was 5.88.

EXAMPLE 13

The reaction mixture (2.0 ml) consisting of 50 mM sodium phosphate buffer at starting pH 7.52, containing 18 mg mannose (50 mM), 50 units of hydrogenase, 12.5 units of GDH, and 1 μmol of $NADP^+$ was placed in a standard laboratory glass pyrex vessel having a thermojacket and heated at 50° C. The reaction was started by the addition of $NADP^+$ and hydrogen evolution was immediately observed.

The reaction vessel was continuously heated at 50° C. until no more hydrogen was produced from the reaction mixture. The ending pH was 7.42.

FIG. 7 gives results of EXAMPLES 14–18 showing rates and yields of hydrogen production from various renewables.

EXAMPLE 14

The reaction mixture (2.0 ml) consisting of 50 mM sodium phosphate buffer at pH 7, containing 34.2 mg lactose (100 μmol), 0.63 units of lactase, 50 units of hydrogenase, 12.5 units of GDH, and 1 μmol of NADP$^+$ was placed in a standard laboratory glass pyrex vessel having a thermojacket and heated at 50° C. The reaction was started by the addition of NADP$^+$ and hydrogen evolution was immediately observed. The reaction vessel was continuously heated at 50° C. until no more hydrogen was produced from the reaction mixture.

EXAMPLE 15

The reaction mixture (2.0 ml) consisting of 50 mM sodium phosphate buffer at pH 7, containing 34.2 mg sucrose (100 μmol), 0.48 units of invertase, 50 units of hydrogenase, 12.5 units of GDH, and 1 μmol of NADP$^+$ was placed in a standard laboratory glass vessel. having a thermojacket and heated at 50° C. The reaction was started by the addition of NADP$^+$ and hydrogen evolution was immediately observed. The reaction vessel was continuously heated at 50° C. until no more hydrogen was produced from the reaction mixture.

EXAMPLE 16

The reaction mixture (2.0 ml) consisting of 50 mM sodium phosphate buffer at pH 7, containing 10 mg glucose/8.4 mg xylose equivalent (111 μmol glucose/xylose equivalent), 38.6 units of avicelase, 50 units of hydrogenase, 12.5 units of GDH, and 1 μmol of NADP$^+$ was placed in a standard laboratory glass vessel having a thermojacket and heated at 50° C. The reaction was started by the addition of NADP$^+$ and hydrogen evolution was immediately observed. The reaction vessel was continuously heated at 50° C. until no more hydrogen was produced from the reaction mixture.

EXAMPLE 17

The reaction mixture (2.0 ml) consisting of 50 mM sodium phosphate buffer at pH 7, containing 20 mg glucose equivalent of starch (111 μmol), 10 units of amyloglucosidase, 50 units of hydrogenase, 12.5 units of GDH, and 1 μmol of NADP$^+$ was placed in a standard laboratory glass vessel having a thermojacket and heated at 50° C. The reaction was started by the addition of NADP$^+$ and hydrogen evolution was immediately observed. The reaction vessel was continuously heated at 50° C. until no more hydrogen was produced from the reaction mixture.

EXAMPLE 18

The reaction mixture (2.0 ml) consisting of 50 mM sodium phosphate buffer at pH 7, containing 20 mg glucose equivalent of steam-exploded aspen starch (111 μmol), 10 units of amyloglucosidase, 50 units of hydrogenase, 12.5 units of GDH, and 1 μmol of NADP$^+$ was placed in a standard laboratory glass vessel having a thermojacket and heated at 50° C. The reaction was started by the addition of NADP$^+$ and hydrogen evolution was immediately observed. The reaction vessel was continuously heated at 50° C. until no more hydrogen was produced from the reaction mixture.

FIG. 8 shows data reflecting the broad sugar specificity of *T. acidophilum* glucose dehydrogenase in hydrogen production.

The liquid form of hydrogen produced by the reaction mixture can also be detected using a redox dye, such as benzyl viologen which turns purple upon reduction. The amount of hydrogen produced is measured spectrophotometrically, such as using a Varian Cary 219 spectrophotometer.

Hydrogen can be produced by the enzymatic method of the present invention, as described in the above examples, in the temperature range from about 20° C. to about 80° C. However, hydrogen may also be produced at lower temperatures if the enzymes utilized in the reactions were derived from microorganisms that live at these lower temperatures but still allow the enzymes to retain sufficient activity at the lower temperatures. In addition, hydrogen may also be produced at higher temperatures if the enzymes utilized in the reactions were derived from microorganisms that live at these higher temperatures but still allow the enzymes to retain sufficient activity at the higher temperatures.

While there has been shown and described what are at present considered the preferred embodiments of the invention, it will be obvious to those skilled in the art that various changes and modifications can be made therein, without departing from the scope of the invention defined by the appended claims.

What is claimed is:

1. An enzymatic method for producing hydrogen comprising the steps of:

a) forming a reaction mixture within a reaction vessel, said reaction mixture comprising an amount of substrate capable of undergoing oxidation within a catabolic reaction, said substrate in an amount sufficient for the production of hydrogen to occur in a stoichiometric yield, an amount of glucose dehydrogenase in an amount sufficient to catalyze said oxidation of said substrate, an amount of hydrogenase sufficient to catalyze an electron-requiring reaction whereby said stoichiometric yield of hydrogen is produced, an amount of pH buffer in an amount sufficient to provide an environment having a pH in the range from 5.0 to 8.0 that allows said hydrogenase and said glucose dehydrogenase to retain sufficient activity for said production of said hydrogen to occur, and an amount of nicotinamide adenine dinucleotide phosphate sufficient to transfer electrons from said catabolic reaction to said electron-requiring reaction;

b) heating said reaction mixture to a temperature in a range from about 20° C. to about 80° C. heating at a temperature sufficient for glucose dehydrogenase and said hydrogenase to retain sufficient activity and at a temperature sufficient for said production of said hydrogen to occur, and heating for a period of time that continues until said hydrogen is no longer produced by said reaction mixture, wherein said catabolic reaction and said electron-requiring reaction have rates of reaction dependent upon said temperature; and c) detecting said hydrogen produced from said reaction mixture.

2. The method of claim 1 wherein said substrate is selected from the group consisting of glucose, galactose, xylose, mannose, sucrose, lactose, cellulose, xylan and starch.

3. The method of claim 1 wherein said reaction mixture further comprises an enzyme that hydrolyzes said substrate into monosaccharide units wherein at least one monosaccharide unit is glucose.

4. The method of claim 3 wherein said enzyme is selected from the group consisting of lactase, invertase, cellulase, amyloglucosidase.

5. The method of claim 1 wherein said glucose dehydrogenase is derived from *Thermoplasma acidophilum*.

6. The method of claim 1 wherein said hydrogenase is derived from *Alcaligenes eutrophus* or from *Pyrococcus funosus*.

7. The method of claim 1 wherein said glucose dehydrogenase is derived from a microbial source that thrives in temperatures below 80° C. and allows said glucose dehydrogenase to retain sufficient activity at said temperatures.

8. The method of claim 1 wherein said glucose dehydrogenase is derived from a microbial source that thrives in temperatures above 60° C. and allows said glucose dehydrogenase to retain sufficient activity at said temperatures.

9. The method of claim 1 wherein said hydrogenase is derived from a microbial source that thrives in temperatures below 100° C. and allows said hydrogenase to retain sufficient activity at said temperatures.

10. The method of claim 1 wherein said hydrogenase is derived from a microbial source that thrives in temperatures above 70° C. and allows said hydrogenase to retain sufficient activity at said temperatures.

* * * * *